US011217345B2

(12) United States Patent
Kadambi et al.

(10) Patent No.: US 11,217,345 B2
(45) Date of Patent: Jan. 4, 2022

(54) ANONYMIZATION OF AUDIO-VISUAL MEDICAL DATA

(71) Applicant: MOCXA Health Private Limited, Mahadevapura (IN)

(72) Inventors: Raja Aditya Kadambi, Mahadevapura (IN); Ankita Kumar, Mahadevapura (IN)

(73) Assignee: MOCXA Health Private Limited, Bangalore (IN)

( * ) Notice: Subject to any disclaimer, the term of this patent is extended or adjusted under 35 U.S.C. 154(b) by 0 days.

(21) Appl. No.: 15/929,817

(22) Filed: May 22, 2020

(65) Prior Publication Data

US 2020/0373002 A1 Nov. 26, 2020

(30) Foreign Application Priority Data

May 22, 2019 (IN) .............................. 201941020360

(51) Int. Cl.
*G06K 9/00* (2006.01)
*G16H 30/40* (2018.01)
*G06F 21/62* (2013.01)
*G06T 7/12* (2017.01)

(52) U.S. Cl.
CPC ......... *G16H 30/40* (2018.01); *G06F 21/6254* (2013.01); *G06K 9/00268* (2013.01); *G06T 7/12* (2017.01)

(58) Field of Classification Search
CPC .................................................. G06F 21/6254
See application file for complete search history.

(56) References Cited

U.S. PATENT DOCUMENTS

| | | | | |
|---|---|---|---|---|
| 6,400,374 B2* | 6/2002 | Lanier | ....................... | G06F 3/14 345/630 |
| 8,126,190 B2* | 2/2012 | Jung | ................... | G06K 9/00771 382/100 |
| 9,799,096 B1* | 10/2017 | De la Torre | .......... | A63F 13/655 |
| 9,836,484 B1* | 12/2017 | Bialynicka-Birula | ...................... | G06F 16/51 |
| 2007/0286520 A1* | 12/2007 | Zhang | .................... | H04N 7/147 382/264 |
| 2012/0007939 A1* | 1/2012 | Michrowski | ........... | H04N 7/147 348/14.07 |
| 2014/0063237 A1* | 3/2014 | Stone | ..................... | H04N 7/181 348/143 |
| 2014/0176663 A1* | 6/2014 | Cutler | ..................... | G06T 5/002 348/14.07 |
| 2015/0213604 A1* | 7/2015 | Li | ....................... | G06K 9/00315 345/473 |

(Continued)

*Primary Examiner* — Hadi Akhavannik
(74) *Attorney, Agent, or Firm* — Schwegman Lundberg & Woessner, P.A.

(57) ABSTRACT

Aspects of anonymization of audio-visual medical data are described. Video data comprising a sequence of images is received for monitoring a subject. One or more faces are detected in each image of the sequence of images. A face of the subject is identified amongst the one or more faces. The identified face is tagged as subject face and remaining faces are tagged as bystander faces. The bystander faces are masked. It is determined whether live monitoring is to be performed for the subject. Based on the determination, the subject face is morphed to obtain anonymized video data, wherein the morphing comprises changing landmark features without changing facial expressions.

19 Claims, 6 Drawing Sheets

(56) References Cited

U.S. PATENT DOCUMENTS

| | | | |
|---|---|---|---|
| 2016/0226985 A1* | 8/2016 | Yoon | H04L 67/36 |
| 2017/0061155 A1* | 3/2017 | Gordon | G06F 21/6254 |
| 2018/0046758 A1* | 2/2018 | Gogin | G06F 21/6254 |
| 2019/0147175 A1* | 5/2019 | Varerkar | H04N 7/155 |
| | | | 726/26 |
| 2019/0377901 A1* | 12/2019 | Balzer | G06F 21/6254 |
| 2019/0378607 A1* | 12/2019 | Chen | G16H 10/60 |
| 2021/0074135 A1* | 3/2021 | Eswara | H04N 7/183 |

\* cited by examiner

ANONYMIZATION OF AUDIO-VISUAL MEDICAL DATA

CLAIM OF PRIORITY

This application claims the benefit of priority to Indian Application No. 201941020360, filed 22 May 2019, which application is incorporated by reference as if reproduced herein and made a part hereof in its entirety, and the benefit of priority of which is claimed herein.

TECHNICAL FIELD

The present subject matter relates in general to anonymization of audio-visual medical data, and in particular, the present invention relates to anonymization for sharing of audio-visual medical data.

BACKGROUND

With technological advancements, audio-visual medical data is increasingly being used by medical practitioners to capture, process, and analyze health-related information. Audio-visual medical data can include, for example, video electroencephalograph (EEG) data in which the EEG records electrical activity of the brain of a patient and simultaneously a video is recorded of the patient to capture the physical manifestation of the brain activity. Video EEG data allows medical practitioners to better diagnose neurological disorders, such as epilepsy. Similarly, in areas such as seizures, movement disorders, gait analysis and many others, video recording of the subject is helpful in better diagnostics and determining new therapies. Sharing of such audio-visual medical data amongst medical practitioners facilitates education, training, and research efforts in geographically distributed locations.

However, strict privacy laws are associated with sharing of health-related information and personally identifiable data. While medical imaging data, such as CT or X-ray data can be shared easily by removing metadata that contains protected health information (PHI) and personally identifiable information to anonymize it, conventional techniques for anonymizing video data result in loss of information and reduce the usefulness of the video data.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
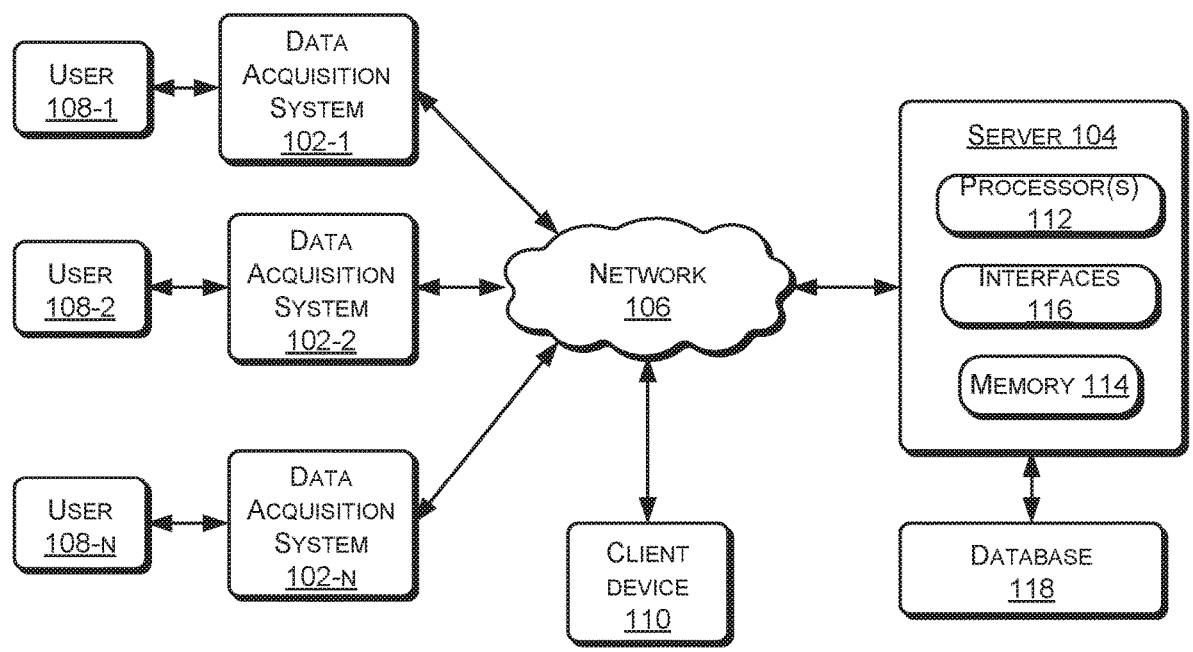
FIG. 1 illustrates an example network environment for anonymization and sharing of audio-visual medical data, in accordance with an implementation of the present subject matter.

The present subject matter disclosed herein relates to anonymization of audio-visual medical data so that it can be shared easily without revealing the identity of persons present in the audio-visual recordings and without loss of relevant medical information. For ease of description, audio-visual medical data is also interchangeably referred to as video medical data herein.

Sharing of video medical data, such as video EEG data, facilitates better diagnosis and discovery of new treatment options. For example, in cases of neurological disorders, medical practitioners can correlate the facial expressions of the patient with the EEG data for better understanding of the disorder. However, since the video medical data includes personally identifiable recordings of the patient, prior consent has to be obtained from the patient before the video medical data can be accessed or shared. Moreover, the video medical data may also include recordings of bystanders, such as care givers or doctors or attendants, who may enter the video frame and get recorded. Such bystanders also have to be contacted and their consent obtained before the video medical data can be shared. This results in large administrative overheads.

In certain cases, live monitoring of the patients may be useful, but may not be possible as the personnel responsible for monitoring will need to obtain consent from everybody who might show up in the video. In case conventional image processing technologies such as blurring/smoothing, or pixelating are used to alter the faces in the video, the information related to facial expressions of the patient is lost and hence the usefulness of the video medical data is substantially reduced.

The present subject matter addresses these and other problems of conventional techniques used to mask the identity of patients or bystanders to enable distributing audio-visual medical data without altering the facial expressions of the patients.

In the facial expressions, generally, the most important thing for the physician is to look for specific movements of landmark features, such as eyes/eyeballs, jaw, mouth, etc. These indicate the true expressions of the face. Hence, in the morphing techniques of the present subject matter, it is ensured that the movements of the landmark features are present without the face itself being recognizable.

The above and other features, aspects, and advantages of the subject matter will be better explained with regard to the following description and accompanying figures. It should be noted that the description and figures merely illustrate the principles of the present subject matter along with examples described herein and, should not be construed as a limitation to the present subject matter. It is thus understood that various arrangements may be devised that, although not explicitly described or shown herein, embody the principles of the present disclosure. Moreover, all statements herein reciting principles, aspects, and examples thereof, are intended to encompass equivalents thereof. Further, for the sake of simplicity, and without limitation, the same numbers are used throughout the drawings to reference like features and components.

FIG. 1 illustrates an example network environment 100 for anonymization and sharing of audio-visual medical data, in accordance with one implementation of the present subject matter. The network environment 100 includes one or more data acquisition systems 102-1, 102-2 . . . 102-n, also referred to as data acquisition system 102. Each data acquisition system 102 is communicatively coupled to a server 104. In one example, the data acquisition system 102 may communicate with the server 104 over a network 106. Further, the data acquisition system 102 may be accessed by one or more users 108-1, 108-2 . . . 108-n, individually referred to as user 108. The user 108 may be a person, such as a patient, whose audio-visual medical data is to be recorded by the data acquisition system 102 and anonymized for storing or for live monitoring. In one example, the anonymized video medical data may be stored at a local computing device (not shown in the figure). In another example, the anonymized video medical data may be stored at the server 104. A client device 110 may also be connected to the server 104 over the network 106 for subsequent retrieval and analysis of the anonymized video medical data provided by the data acquisition system 102.

In one example, the data acquisition system 102 can be implemented as a computing device, a laptop, a desktop, a mobile computing device, and the like. The data acquisition system 102 can be used to acquire video medical data of the user 108 and process the video medical data for anonymization and sharing. The user 108 may be, for example, a patient admitted to a hospital or present at a remote location and the audio-visual medical data is to be captured and shared with other persons, such as medical practitioners, or is to be monitored live at the same location or from a remote location. It will be understood that while various example implementation scenarios are discussed herein, other possible implementation scenarios will also be evident from the teachings of the present subject matter and are intended to be covered by the present disclosure.

To enable anonymization without loss of medically relevant data, the present subject matter facilities automatically de-identifying the patient's face by morphing the features rather than blurring/pixelating so that facial expressions of the patient remain recognizable. Additionally, it also provides for detecting bystanders and masking their faces automatically.

In one example, the data acquisition system 102 may identify the subject, i.e., the user or patient, and bystanders, i.e., other persons, in the video medical data. In one example, object recognition techniques may be used to identify faces in the video medical data. As used herein, identification of a face refers to detection with or without facial recognition. In case there are multiple faces, the subject may be identified based on, for example, position of the face in the video, length of time the face is present in the video, tracking of the faces, and the like. In one example, the face present generally in the foreground of the video may be identified as the subject and faces in the background may be identified as bystanders. In another example, the face of a person who is lying down on a bed may be identified as the subject. In yet another example, the face that is present in the video for the most length of time may be identified as the subject. It will be understood that other considerations may also be used for identifying the subject. Accordingly, the faces may be tagged as subject face or bystander face.

Further, the data acquisition system 102 may morph the face of the subject so that while the identity of the subject gets masked, the facial expressions of the subject are still recognizable and can be used for subsequent analysis. Additionally, the data acquisition system 102 may mask the face of the bystanders, for example, by blurring or pixelating, so that the identity of the bystanders is also masked. The audio-visual medical data thus obtained may be referred to as anonymized video medical data.

The anonymized video medical data may be used for live monitoring or for storage and subsequent analysis. In one example, in the case of live monitoring the subject's face may not be morphed, however, the bystanders' faces may be masked.

Thus, the video medical data can be processed by the data acquisition system 102 so that the persons in the video medical data are no longer identifiable, but the medically relevant information is still retained. As will be understood, the data acquisition system 102 will include various hardware and software components for its functioning. Example implementations and operations of the data acquisition system 102 will be discussed in detail with reference to FIG. 2.

In one example, the data acquisition system 102 can share the anonymized video medical data with the server 104, over the network 106, for live monitoring or storage. The network 106 can be an individual network or a collection of computers, servers, mainframes, network devices, peripherals, or other devices connected to each other for sharing of data, e.g., Internet or Intranet. The network 106 can include different types of networks, such as, a peer-to-peer network, a server/domain network, a local area network, a wide-area network, or a combination thereof. Accordingly, the network 106 includes various topologies, such as mesh, star, tree, bus, point-to-point and network entities, such as servers, routers, gateways; however, such details have been omitted for brevity.

The server 104 may include processor(s) 112, memory 114, and interfaces 116. Further, the server 104 may be in communication with a database 118. In various implementations, the database 118 may be an operational database or a data warehouse.

The processors 112 may be implemented as one or more microprocessors, microcomputers, microcontrollers, digital signal processors, central processing units, state machines, logic circuitries, and/or any devices that manipulate signals based on operational instructions. Among other capabilities, the processors 112 can fetch and execute computer-readable instructions stored in a memory, such as memory 114.

The memory 114 may include any non-transitory computer-readable medium including, for example, volatile memory (e.g., RAM), and/or non-volatile memory (e.g., EPROM, flash memory, etc.). The memory 114 may include an external memory unit, such as a flash drive, a compact disk drive, an external hard disk drive, or the like.

The interfaces 116 may include a variety of computer-readable instructions-based interfaces and hardware interfaces that allow interaction with other communication, storage, and computing devices, such as network entities, web servers, databases, and external repositories, and peripheral devices. The interfaces may also include input/output (I/O) interfaces, such as display screens, keyboards, touch screens, and the like.

In one example, the server 104 can receive the anonymized audio-visual medical data from the data acquisition system 102 and can further process it for enhanced data security prior to storage in the database 118. For example, based on instructions stored in the memory 114, the processor 112 can encrypt the anonymized video data and/or add a date and time stamp or other metadata to the anonymized video data before storing it in the database 118. In other examples, the server 104 may store the anonymized video data as received from the data acquisition system 102.

Subsequently, the client device 110 can communicate with the server 104 to retrieve and analyze the videos of patients for accurate diagnosis of medical conditions. As the server 104 may receive and store anonymized video medical data from geographically dispersed facilities and for multiple users, it can facilitate study of different subjects and their symptoms to devise more effective treatment options. In one example, the client device 110 may be used by different medical institutions and practitioners to gain access to the anonymized video medical data stored in the database 118, thus allowing a large amount of anonymized video medical data to be used for research and educational purposes. In other examples, the client device 110 can be used to obtain the anonymized video medical data and share it with other medical institutions over the network 106.

Figure 2:
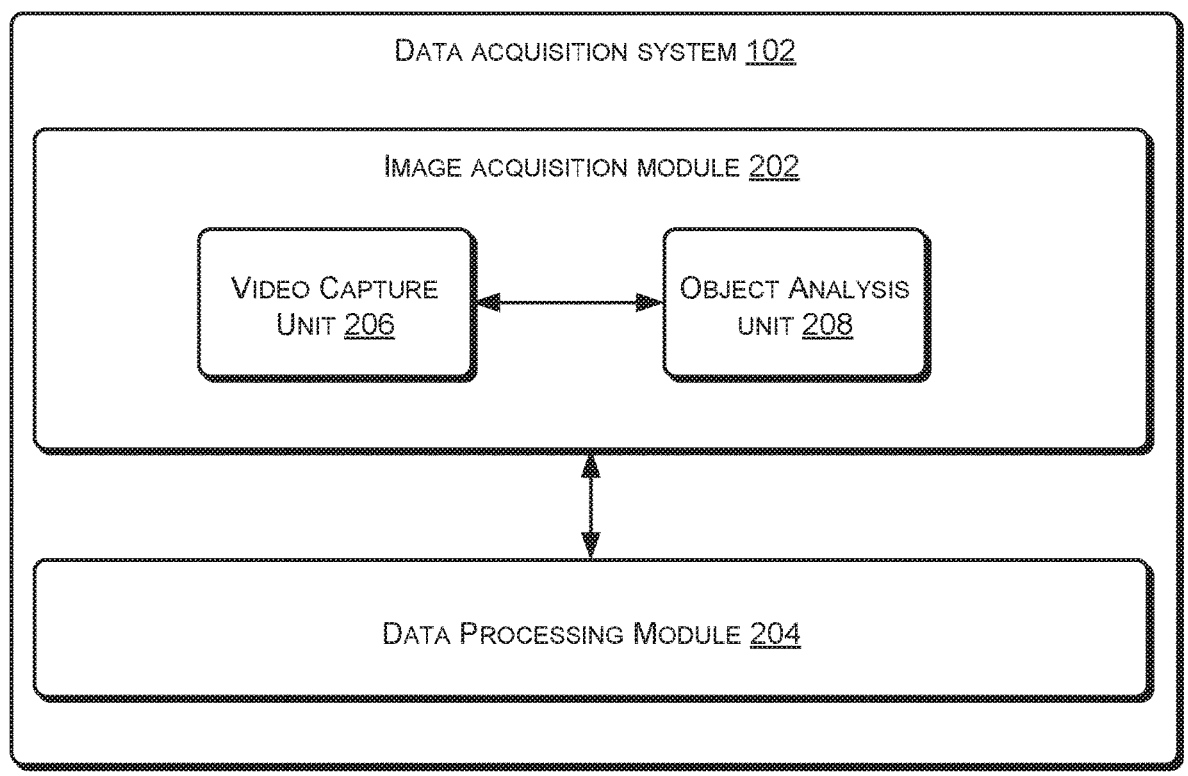
FIG. 2 illustrates a block diagram of a data acquisition system, in accordance with an implementation of the present subject matter.

FIG. 2 illustrates a block diagram of a data acquisition system 102, in accordance with an implementation of the present subject matter. The data acquisition system 102 includes an image acquisition module 202 and a data processing module 204 in communication with each other. In one example, the image acquisition module 202 and the data processing module 204 can communicate through application programming interfaces. Though not shown, the data acquisition system 102 may include various hardware and software components, such as processor, memory, and interfaces, similar to the server 104.

Further, the image acquisition module 202 and the data processing module 204 can be implemented as a combination of hardware and software components to achieve the desired functionality as would be understood by a person skilled in the art based on the teachings of the present subject matter.

In one implementation, the image acquisition module 202 includes a video capture unit 206 and an object analysis unit 208 in communication with each other, for example, through application programming interfaces. In one example, the video capture unit 206 may be a camera that is connected to or integrated with the data acquisition system 102 and includes applications that drive or control the camera, such as audio and video drivers.

In operation, the video capture unit 206 can obtain a video of a user 108, who is the subject, for example, in the form of a sequence of images also referred to as video frames. In one example, a tracking device may be placed on the head of the user 108 and the video capture unit 206 may include a sensor to track the user 108 through the tracking device so that the face of the subject remains in the video frame, preferably in the centre of the video frame, even if the user 108 moves around in the vicinity of the video capture unit 206. For example, the tracking device may be an infra-red (IR) emitter and the video capture unit 206 may include or be connected to an IR sensor for tracking the user while capturing the video. In another example, the video capture unit 206 may implement facial tracking for tracking the user. The video capture unit 206 forwards the video frames to the object analysis unit 208.

The object analysis unit 208 can receive the video frames and perform object segmentation, detection, and tracking operations and can provide feedback to the video capture unit 206. The object analysis unit 208 may first perform object segmentation to identify different objects, for example, based on a shape or an appearance representation of the objects or a combination thereof. The object segmentation can be done using any known technique. From the segmented image, the object analysis unit 208 can identify or detect faces in the image. The detection of faces may be done using techniques known in the art, for example, based on features or templates and the like.

In addition, the object analysis unit 208 can distinguish the face of the subject from those of bystanders and then track the face of the subject. In one example, the face who appears for the longest time in the video is identified as the subject. For this, the face that is present in the most number of consecutive images among a predetermined number of consecutive images may be identified as the subject face. In another example, as the subject may be typically lying on the bed or prone, the orientation of the subject made be used for the identification of the subject. For this, the face of a person identified as lying on a horizontal surface may be identified as the subject face. In yet another example, position of the face in the video frame may be used to identify the subject as the subject's face is expected to be situated around the center of the video frame. For this, a face that is present in foreground portion of the images may be selected as the subject face or a face that is present around the center of the video frame may be selected as the subject face. In yet another example, the object analysis unit 208 may also perform facial recognition based on prestored images of the subject to identify the subject face. As will be understood, the pre-stored images may be securely stored locally in the data acquisition system 102 and hence the subject's privacy may not be compromised in any way.

In one example, the object analysis unit 208 may also provide an indication, such as a dotted-line box on a display of the data acquisition system 102 to indicate the face that has been identified as the subject's face. The user 108 may be asked to confirm the identification.

After the subject is identified, the faces are tagged as subject or bystander face and the bystanders' faces are marked for masking, such as by blurring or pixelation or other prior art techniques. Since the facial expressions of the bystanders are not to be considered, any loss of information is inconsequential.

As the subject may move after the identification has happened, the object analysis unit 208 may track the subject's face to follow it and continually distinguish it from others in the video. The object analysis unit 208 may also provide feedback to the video capture unit 206 to ensure that the subject is properly tracked. Thus, the object tracking may be done by the video capture unit 206 or the object analysis unit 208 or both. In one example, object tracking can be done using any known techniques like point tracking, kernel tracking, silhouette tracking, and the like. In another example as discussed above, the user 108 may wear a sensor or indicator, such as IR transmitter, that may be tracked by the object analysis unit 208.

The data processing module 204 can obtain the analyzed images from the object analysis unit 208 of the image acquisition module 202. The analyzed images include tags or indicators that indicate the faces and mark them as subject face or bystander face. The data processing module 204 can then mask the faces of the bystanders and de-identify the face of the subject by morphing. The morphing may be performed such that the landmark features of the subject are changed so that the subject is unrecognizable or anonymized, without changing facial expressions which are critical for subsequent analysis. For morphing the subject's face, landmark features (also referred to as landmarks) may be first identified using techniques known in the art. The landmarks provide the ability to detect and localize parts of the face including, eyes, eyebrows, mouth, jaws, nose, etc. These specific localization points give accurate representation of expressions and have to be retained without distortion or with minimal distortion. For instance, rapid eye blink might represent one kind of seizure, complete lack of eye movements might represent another kind of seizure or neurological condition. In addition to eyes, the position and movement of eyeballs is very important as well for seizure analysis. Similarly, mouth movements and jaw movements can give information about different neurological conditions and form part of facial expressions that have to be retained.

In one example, for morphing the subject face, the basic texture and size of the landmarks may be changed such that the relative change from image-to-image is retained. For example, the eye texture and size may be changed by enlarging it while at the same time applying techniques to change the facial textures, skin smoothing. This may be done by changing the pixels of the features in the image. In case the subject eyes get enlarged during a seizure, the eye size in the morphed image gets further enlarged to replicate accurately the changed facial expression of the subject. Thus, during morphing, it is ensured that the face is changed without making it look dysmorphic and the relative changes in landmark features are accurately captured and retained.

In another example, once the landmark features of the subject's face are identified, the landmarks are normalized and copied onto an artificial subject's face to obtain a morphed subject's face. In an example, the artificial subject's face can be generated using a deep machine learning model such as StyleGAN™. The morphed subject's face thus obtained retains the original orientation as well as facial expressions of the subject. The morphed subject's face is then overlaid over the subject's face in the image or video frame. This is done for each image or frame so that the change in facial expression over the different images is visible. For example, if the eyes change in size or the jaw makes a particular motion, the same change in size and motion are also visible in the morphed subject's face in the video. As the morphed subject's face in the video medical data is created by using the deep machine learning model and does not belong to anyone in the real world, it therefore ensures complete anonymization of the source subject. Moreover by overlaying the subject face with the morphed subject face, the change in facial expressions can be observed along with any change in motion of the body of the subject.

Thus, using the techniques of the present subject matter, the facial expressions are retained intact and the critical landmarks of the face such as the eyes and mouth are not changed very much except in size or texture to de-identify the subject. Thus, an anonymized video data is obtained for sharing and subsequent analysis.

In one example, if live monitoring is to be performed, the data processing module 204 may mask the faces of bystanders without morphing the face of the subject to obtain the anonymized video data for sharing for live monitoring.

Figure 3A:
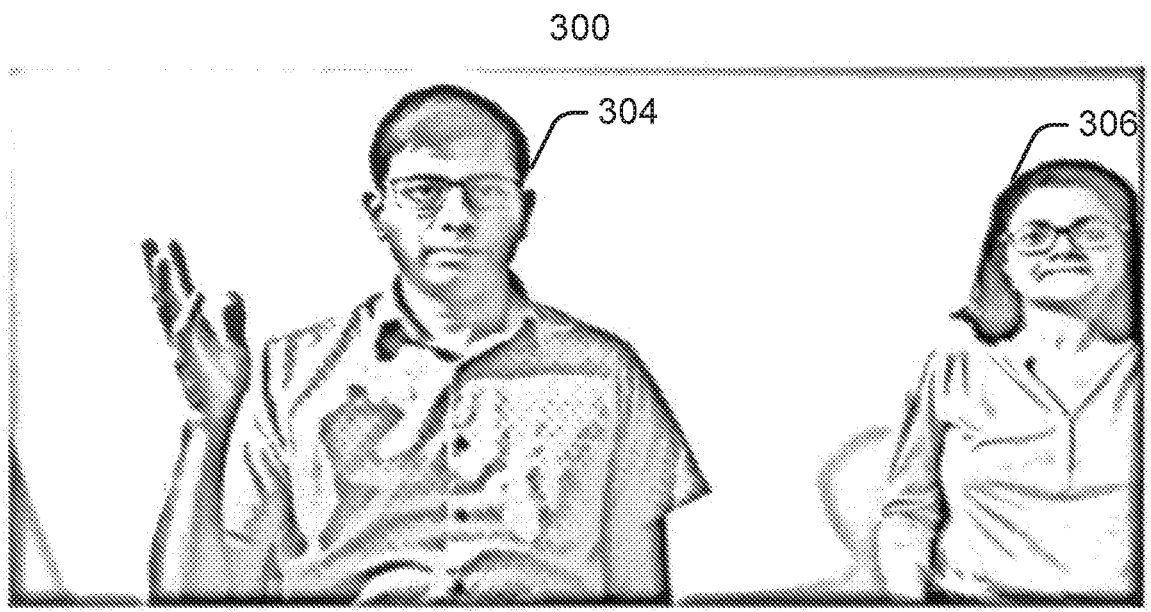
FIG. 3(a) depicts an image frame of a video, with a subject and bystander, captured for anonymization and sharing of audio-visual medical data, in accordance with an implementation of the present subject matter.
Figure 3B:
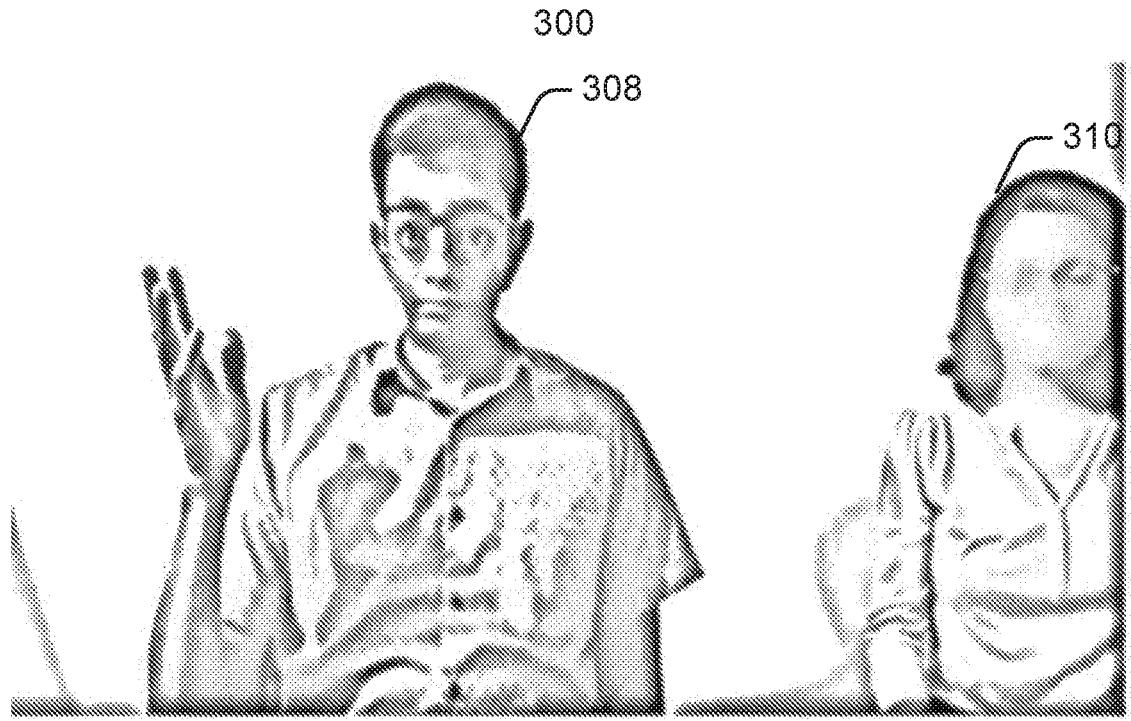
FIG. 3(b) depicts the image frame of FIG. 3(a) after anonymization, in accordance with an implementation of the present subject matter.

FIG. 3(a)-3(b) illustrate the first technique for morphing that may be performed by data processing module 204, where the landmark features of a subject's face are modified in each frame or image without modifying the facial expression. FIG. 3(a) illustrates an image 300 of a subject and a bystander as captured, and FIG. 3(b) illustrates an image 302 of the subject with a morphed face and the bystander with masked face in accordance with an example of the present subject matter.

In image 300, a subject 304 with a bystander in the background 306 have been captured. The image 300 can be a video frame received from the video capture unit 206 of the image acquisition module 202. In an example, an image 300 can be part of a video stream captured by the video capture unit 206 for live monitoring of patients for their accurate medical diagnosis.

After processing of the image 300, for example, by the data processing module 204, the image 302 may be obtained with the morphed subject's face 308 and the masked face of bystander 310. Thus, in the morphing that is done by the first technique, the size and texture of landmark features are changed in the image by modifying the image pixels directly, but without changing the facial expressions.

Figure 4A:
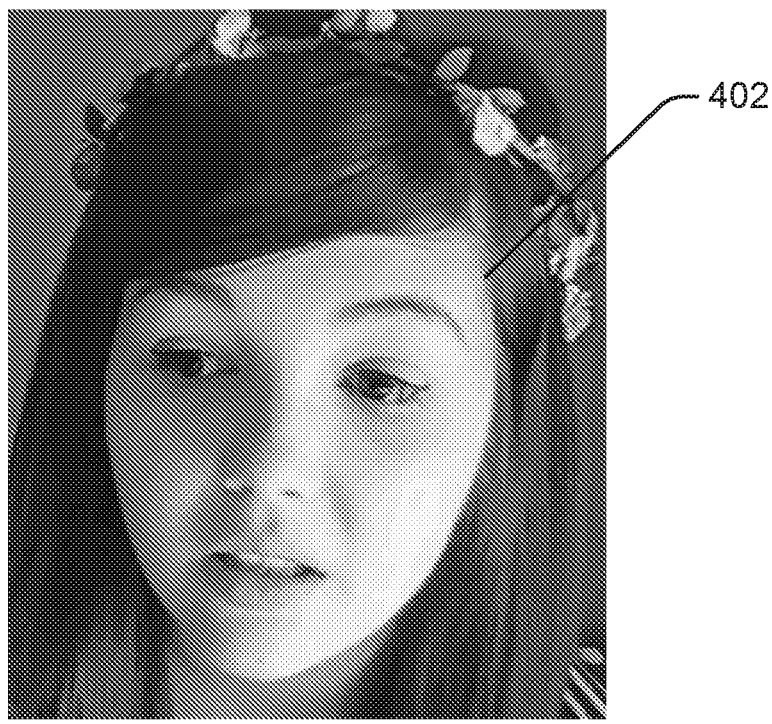
FIG. 4(a) depicts an image, with a source subject's face captured for anonymization, in accordance with an implementation of the present subject matter.
Figure 4B:
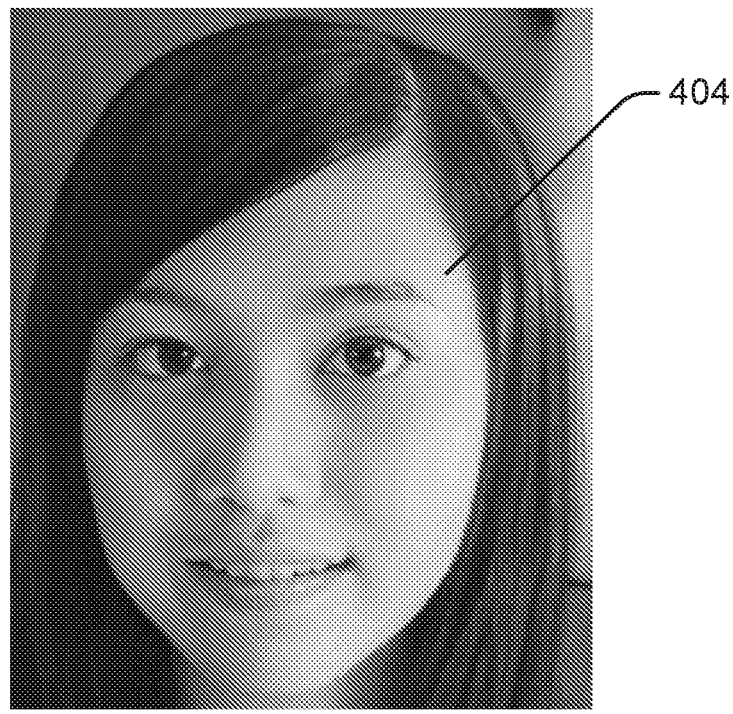
FIG. 4(b) depicts an image, with an artificial subject's face generated for anonymization, in accordance with an implementation of the present subject matter.
Figure 4C:
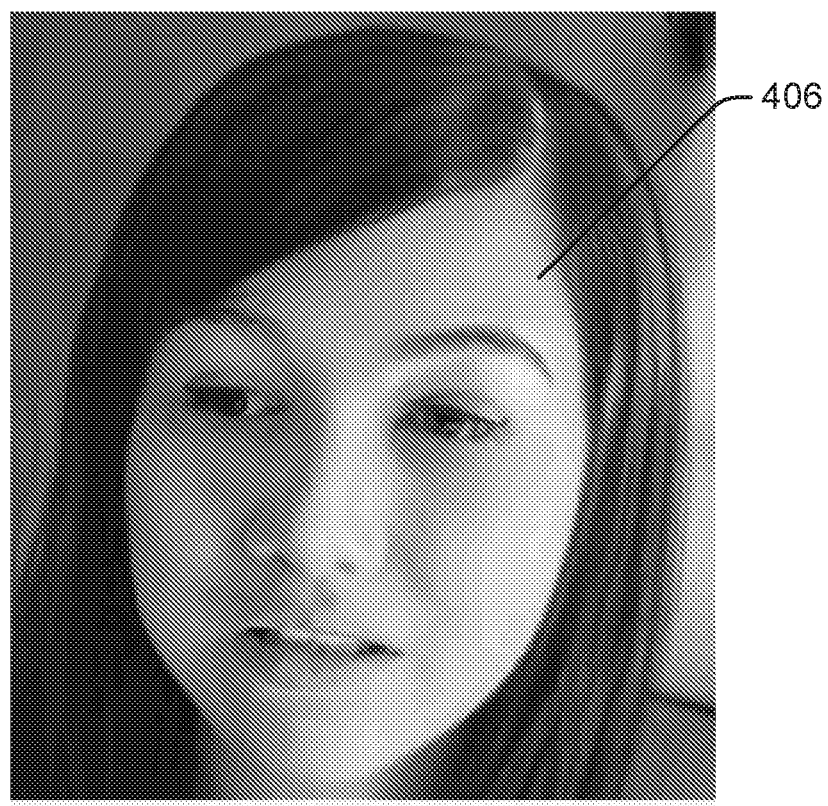
FIG. 4(c) depicts an image where the landmarks of source subject's face of FIG. 4(a) is morphed on to the artificial subject's face of FIG. 4(b) after anonymization to obtain a target subject's face, in accordance with an implementation of the present subject matter.

FIG. 4(a)-4(c) illustrate the second technique for morphing that may be performed by data processing module 204, where the landmark features of a subject's face are translated onto an artificial face to obtain a morphed subject's face, which is then overlaid onto the subject face. For discussion purpose, the original subject is also referred to as source subject and the morphed subject is also referred to as target subject.

FIG. 4(a) depicts an image, with a source subject's face 402 captured for anonymization, in accordance with an implementation of the present subject matter. The image can be from a video frame received from the video capture unit 206 of the image acquisition module 202. Landmarks such as eyes, eyebrows, mouth, jaw, nose, etc., of the source subject's face 402 are identified. In an example, landmarks may be identified using techniques known in the art. The landmarks provide the ability to detect and localize the movement of parts of the original subject's face such as closed eyes, open eyes, blink detection, movement of mouth, etc. These specific localization points provide an accurate representation of facial expressions. For instance, rapid eye blink may represent one kind of seizure, complete lack of eye movements may represent another kind of seizure or neurological condition. The same can be said for mouth movements and jaw movements as well.

FIG. 4(b) depicts an image, with an artificial subject's face 404 generated for anonymization, in accordance with an implementation of the present subject matter. In an example, the artificial subject's face is generated using a deep machine learning model such as StyleGAN™. In another example, the artificial subject face can be obtained from a list of volunteers who have given prior consent for usage. These faces of volunteers are pre-acquired and stored in the database for anonymization.

FIG. 4(c) depicts an image where the landmarks of the source subject's face 402 of FIG. 4(a) are morphed on to the artificial subject's face 404 of FIG. 4(b) to obtain a target subject's face 406 after anonymization, in accordance with an implementation of the present subject matter. The morphing may be performed such that the landmark features of the source subject are changed so that the source subject is unrecognizable or anonymized, without changing facial expressions which are critical for subsequent analysis.

To this end, the landmarks of artificial subject's face are detected, and the corresponding landmarks of source subject's face are also extracted. For example, considering the landmarks of the left eye of the artificial subject and source subject are detected. Further, the left eye landmarks of source subject are normalized in such a way that it matches the coordinates of the artificial subject's face. This can be done by a linear transformation operation. The left eye landmarks from the source subject's face are extracted and warped as per the normalization requirements. The warped left eye of the source subject's face is then pasted on the artificial subject's coordinates. Similarly, the same can be done for the remaining landmarks of the source subject's face such as the right eye, mouth, jaw etc., and for all frames of the video medical data. Finally, the frames of video medical data are stitched together. The target subject's face thus obtained retains the original orientation as well as facial expressions of the source subject in the video medical data. Since the target subject face may not belong to anyone in the real world, it therefore ensures complete anonymization of the subject.

Figure 5:
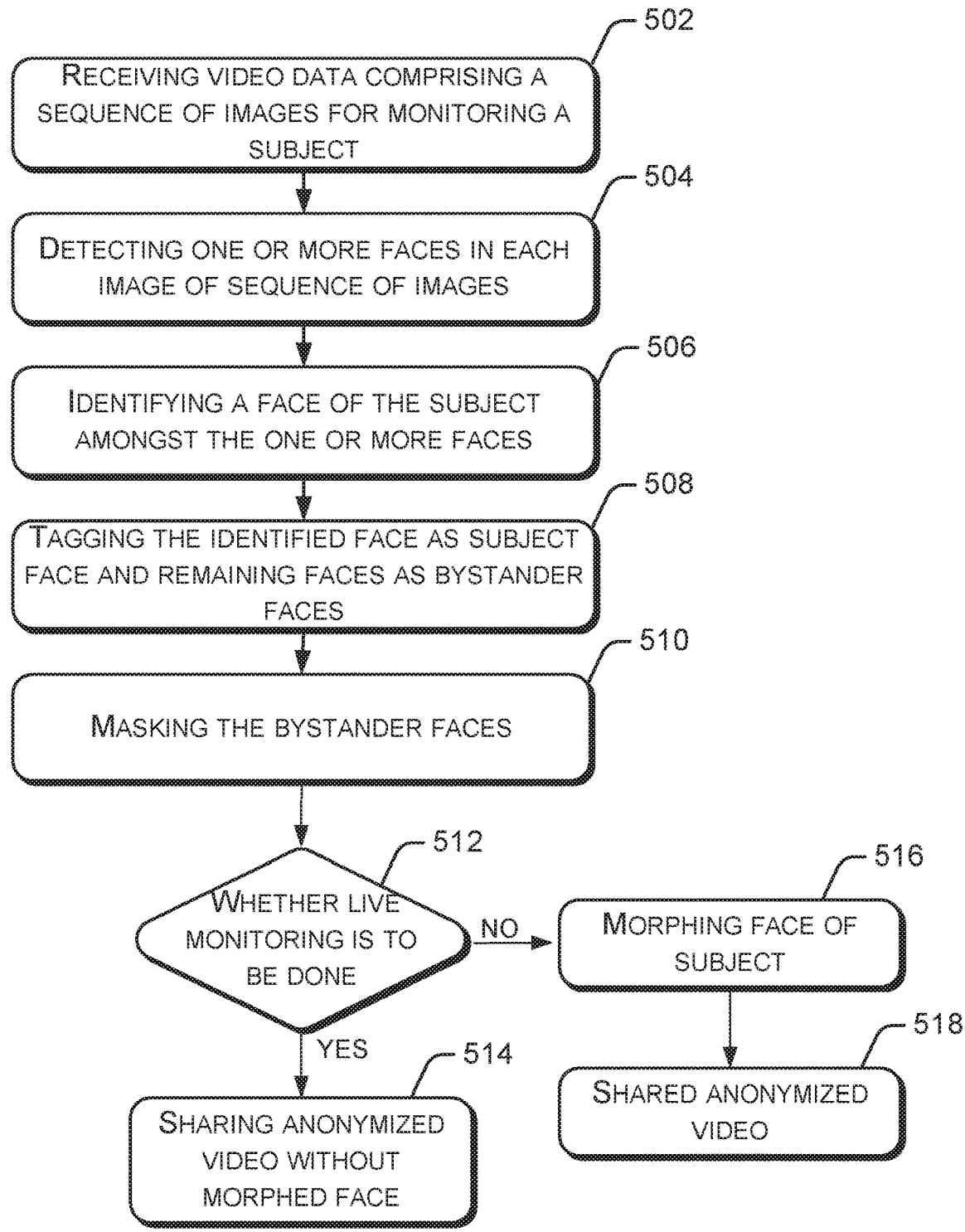
FIG. 5 illustrates a method for anonymization and sharing of audio-visual medical data, in accordance with an implementation of the present subject matter.

FIG. 5 illustrates an example method 500 for anonymization and sharing of audio-visual medical data, in accordance with principles of the present subject matter. A person skilled in the art will readily recognize that steps of the method 500 can be performed by programmed computing devices. The method 500 may be implemented in any suitable hardware, computer readable instructions, firmware, or combination thereof. Herein, some examples are also intended to cover program storage devices and non-transitory computer readable medium, for example, digital data storage media, which are computer readable and encode computer-executable instructions, where said instructions perform some or all of the steps of the described methods. The program storage devices may be, for example, digital memories, magnetic storage media, such as magnetic disks and magnetic tapes, hard drives, or optically readable digital data storage media.

With reference to method 500, as illustrated in FIG. 5, at block 502, video data can be received, for example, from a video capture unit. The video data comprises a sequence of images for monitoring a subject. In one example, the video data may include the subject or user, such as a patient, and bystanders, such as medical practitioners. The video is to be anonymized and shared for live monitoring or for storage and subsequent analysis.

At block 504, in each image of the sequence of images of the video data, faces are detected. In an example, the detection of faces can be done by the object analysis unit 208 of the image acquisition module 202.

At block 506, the face of the subject is identified from among the faces identified. For example, the face that is in the foreground of the image may be identified as the subject. In other examples, other parameters as discussed earlier may be used for detecting the subject. In one example, the face identification and tracking of a subject's face can be done by the object analysis unit 208 of the image acquisition module 202.

At block 508, identified face is tagged as subject face and the remaining faces in the sequence of images, other than the subject, are tagged as bystanders. For example, the detection of the faces of the subject and bystanders can be done by the object analysis unit 208.

At block 510, the bystander's faces can be masked after detection. In an example, the bystander's faces can be blurred or pixelated to mask their identity. The masking may be performed, for example, by the data processing module 204.

At block 512, it is determined whether live monitoring is to be performed. For example, a user or a medical practitioner may select an option for live monitoring when the data acquisition system 102 is to be used.

If live monitoring is to be performed, then the method moves to block 514, where an anonymized video can be shared with only the masking of the bystanders' faces and without morphing of subject's face.

If live monitoring is not to be performed, then the method moves to block 516, where the de-identification of a subject's face can be done. In an example, a patient's face can be morphed or de-identified for anonymization of video medical data. The morphing can be done by the first technique discussed above, for example, by changing the size and texture of features, such as eyes and mouth, of the subject's face, without loss of facial expression. The morphing may be alternatively performed by the second technique discussed above by normalizing and copying the landmark features from the subject's face onto an artificial face to obtain a morphed subject's face and overlaying the morphed subject's face on the subject's face.

At block 518, the anonymized video, having the morphed face of the subject and masked faces of the bystanders is shared, for example, with server 104. The anonymized video can be stored and distributed, for example, with various medical practitioners or institutions, for training, research, and educational purposes.

Thus, the present subject matter allows for data sharing of audio-visual information. This removes the subjectivity inherent in current methods that use textual interpretation by the medical practitioners due to inability to share audio-visual information. Further, real videos of patients with de-identified data can be used for medical teaching of physicians, technicians. This leads to better knowledgeable staff and medical teams and continuous education is also made possible.

Moreover, during clinical trials, data, conventionally, data was shared textually or not shared at all, or, in many cases, the monitors had to visit local sites to view video information. However, as per the teachings of the present subject matter, since the de-identified or anonymized audio-visual data can be shared easily over standard encrypted mediums via the Internet, it can lead to more efficient drug discovery. Further, live video monitoring, such as for ICU patients, is now possible without revealing identity of bystanders.

Although implementations for anonymization and sharing of audio-visual medical data have been described in language specific to structural features and/or methods, it is to be understood that the invention is not necessarily limited to the specific features or methods described. Rather, the specific features and methods are disclosed and explained in the context of a few example implementations.

We claim:

1. A system for anonymization of audio-visual medical data, the system comprising:
   a processor;
   an object analysis unit executable by the processor to:
      receive video data comprising a sequence of images for monitoring a subject;
      detect one or more faces in each image of the sequence of images;
      identify a face of the subject amongst the one or more faces; and
      tag the identified face as subject face and remaining faces as bystander faces; and
   a data processing module executable by the processor to:
      mask the bystander faces;
      determine whether live monitoring is to be performed for the subject;
      when live monitoring is to be performed, retain the subject face without morphing and provide the video data with the masked bystander faces and retained subject face for live monitoring; and when live monitoring is not to be performed, morph the subject face to obtain anonymized video data, wherein the morphing comprises changing landmark features without changing facial expressions, and provide the anonymized video data with the masked bystander faces and morphed subject face for storage.

2. The system of claim 1, comprising a video capture unit to capture the video data of the subject.

3. The system of claim 2, wherein the video capture unit comprises a sensor to track the subject during video capture to keep the subject in a field of view of the video capture unit.

4. The system of claim 1, wherein, to detect the one or more faces in an image, the object analysis unit is to segment the image into objects and detect the one or more faces in the objects.

5. The system of claim 4, the object analysis unit is executable to identify the face of the subject based on one or more of:

performing face recognition to recognize the face of the subject;

selecting a face that is present in foreground portion of the images as the subject face;

selecting a face that is present around the center of the video frame;

selecting a face that is present in the most number of consecutive images among a predetermined number of consecutive images as the subject face; and selecting a face of a person identified as lying on a horizontal surface as the subject face.

6. The system of claim 1, wherein the object analysis unit is executable to track the subject face in the sequence of images.

7. The system of claim 1, wherein the data processing module is executable to mask the bystander faces by blurring or pixelation.

8. The system of claim 1, wherein the data processing module is executable to morph the subject face by changing size or texture or both of one or more landmark features.

9. The system of claim 1, wherein the data processing module is executable to morph the subject face by:

normalizing and copying landmark features from the subject face to an artificial face to obtain a morphed subject face; and overlaying the morphed subject face on the subject face.

10. The system of claim 1, wherein the data processing module is executable to morph the subject face in each image of the sequence of images to store the anonymized video data for sharing and analysis.

11. A method for anonymization of audio-visual medical data, the method comprising:

receiving video data comprising a sequence of images for monitoring a subject;

detecting one or more faces in each image of the sequence of images;

identifying a face of the subject amongst the one or more faces;

tagging the identified face as subject face and remaining faces as bystander faces;

masking the bystander faces;

determining whether live monitoring is to be performed for the subject;

when live monitoring is to be performed, retaining the subject face without morphing and providing the video data with the masked bystander faces and retained subject face for live monitoring; and when live monitoring is not to be performed, morphing the subject face to obtain anonymized video data, wherein the morphing comprises changing landmark features without changing facial expressions, and providing the anonymized video data with the masked bystander faces and morphed subject face for storage.

12. The method of claim 11, wherein detecting the one or more faces in an image comprises segmenting the image into objects and detecting the one or more faces in the objects.

13. The method of claim 11, wherein identifying the face of the subject comprises one or more of:

performing face recognition to recognize the face of the subject;

selecting a face that is present in foreground portion of the images as the subject face;

selecting a face that is present around the center of the video frame;

selecting a face that is present in the most number of consecutive images among a predetermined number of consecutive images as the subject face; and selecting a face of a person identified as lying on a horizontal surface as the subject face.

14. The method of claim 11 comprising, tracking the subject face in the sequence of images.

15. The method of claim 11, wherein the masking of bystander faces comprises blurring or pixelating the bystander faces.

16. The method of claim 11, wherein the morphing the subject face comprises changing size or texture or both of one or more landmark features.

17. The method of claim 11, wherein the morphing the subject face comprises:

normalizing and copying landmark features from the subject face to an artificial face to obtain a morphed subject face; and overlaying the morphed subject face on the subject face.

18. A non-transitory computer readable medium comprising instructions that when executed by a processor cause the processor to:

obtain video data comprising a sequence of images for monitoring a subject;

detect one or more faces in each image of the sequence of images;

identify a face of the subject amongst the one or more faces;

tag the identified face as subject face and remaining faces as bystander faces;

mask the bystander faces;

obtain a first anonymized video data comprising masked bystander faces and unchanged subject face for live monitoring; and obtain a second anonymized video data comprising masked bystander faces and morphed subject face by morphing the subject face in the sequence of images for storing the second anonymized video data for sharing and analysis, wherein the morphing the subject face comprises:

changing size or texture or both of one or more landmark features of the subject face without changing facial expressions of the subject face; or overlaying the subject face with a morphed subject face, wherein the morphed subject face is obtained by normalizing and copying landmark features of the subject face onto an artificial face.

19. The non-transitory computer readable medium of claim 18 further comprising instructions that when executed by the processor cause the processor to identify the face of the subject based on one or more of:
- performing face recognition to recognize the face of the subject;
- selecting a face that is present in foreground portion of the images as the subject face;
- selecting a face that is present around the center of the video frame;
- selecting a face that is present in the most number of consecutive images among a predetermined number of consecutive images as the subject face; and
- selecting a face of a person identified as lying on a horizontal surface as the subject face.

* * * * *